United States Patent [19]

Bauer et al.

[11] 4,341,229

[45] * Jul. 27, 1982

[54] METHOD AND APPARATUS FOR SETTING HAIR

[75] Inventors: Daniel Bauer, Le Raincy; Jules Leroy, Blanc Mesnil; Jean-Paul Beck, Paris, all of France

[73] Assignee: L'Oreal, Paris, France

[*] Notice: The portion of the term of this patent subsequent to Sep. 4, 1996, has been disclaimed.

[21] Appl. No.: 951,458

[22] Filed: Oct. 16, 1978

Related U.S. Application Data

[62] Division of Ser. No. 584,980, Jun. 8, 1975, Pat. No. 4,166,473.

[51] Int. Cl.³ .............................................. A45D 7/00
[52] U.S. Cl. ..................................................... 132/7
[58] Field of Search ............................ 132/7, 9, 33 R; 219/225

[56] References Cited

U.S. PATENT DOCUMENTS 1,504,567  8/1924  MacDonald et al. ............ 132/33 R
4,166,473  9/1979  Bauer et al. ....................... 132/37 R Primary Examiner—G. E. McNeill
Attorney, Agent, or Firm—Brisebois & Kruger

[57] ABSTRACT

Method and apparatus for setting hair by successively passing steam and cooling air through said hair while wound on rollers.

5 Claims, 22 Drawing Figures

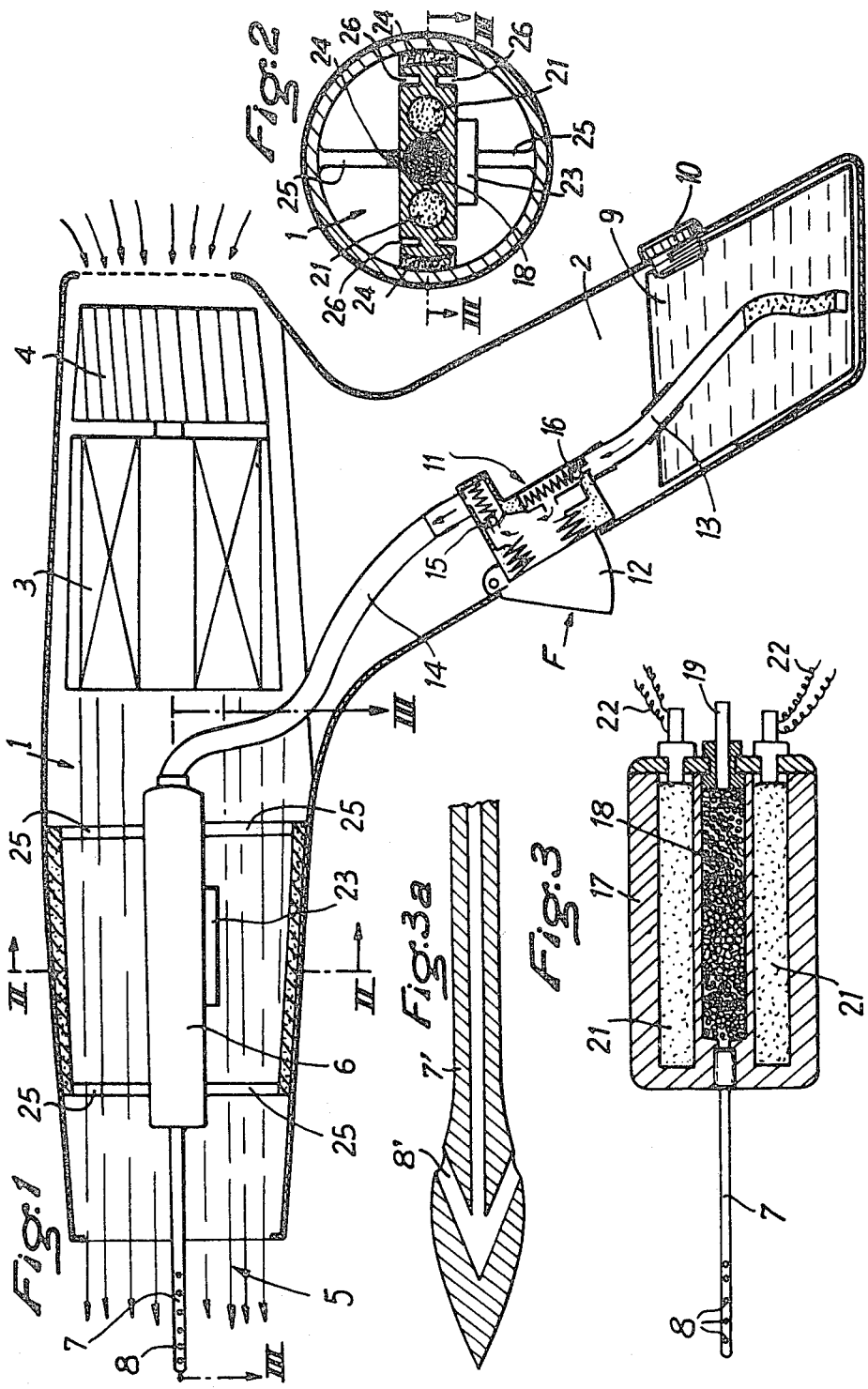

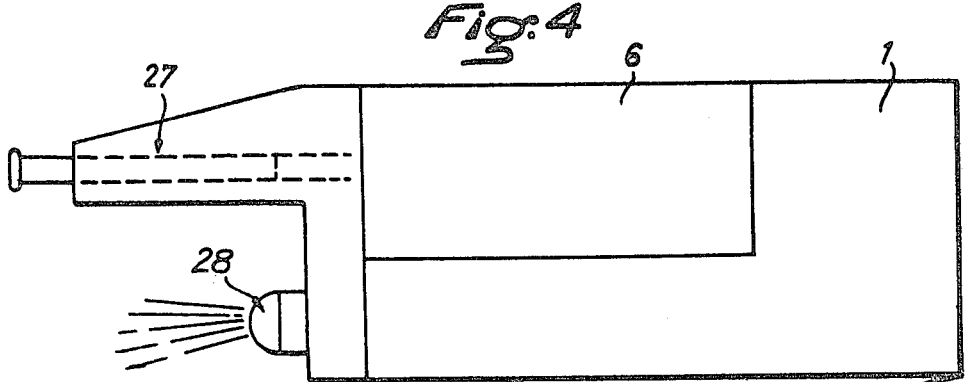
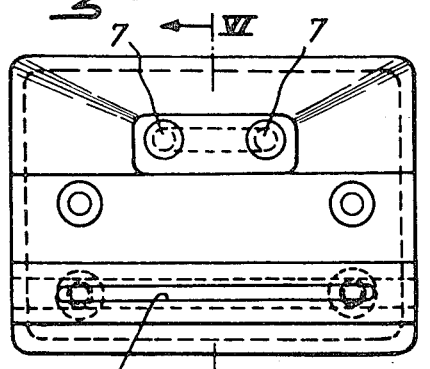
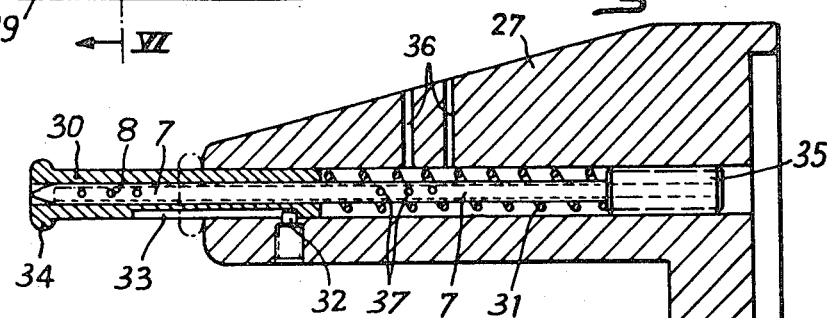
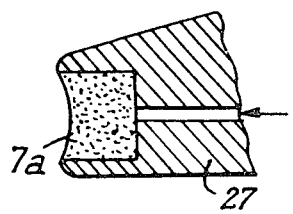
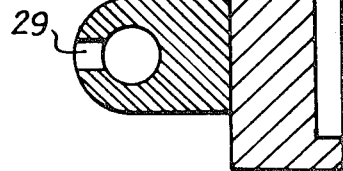

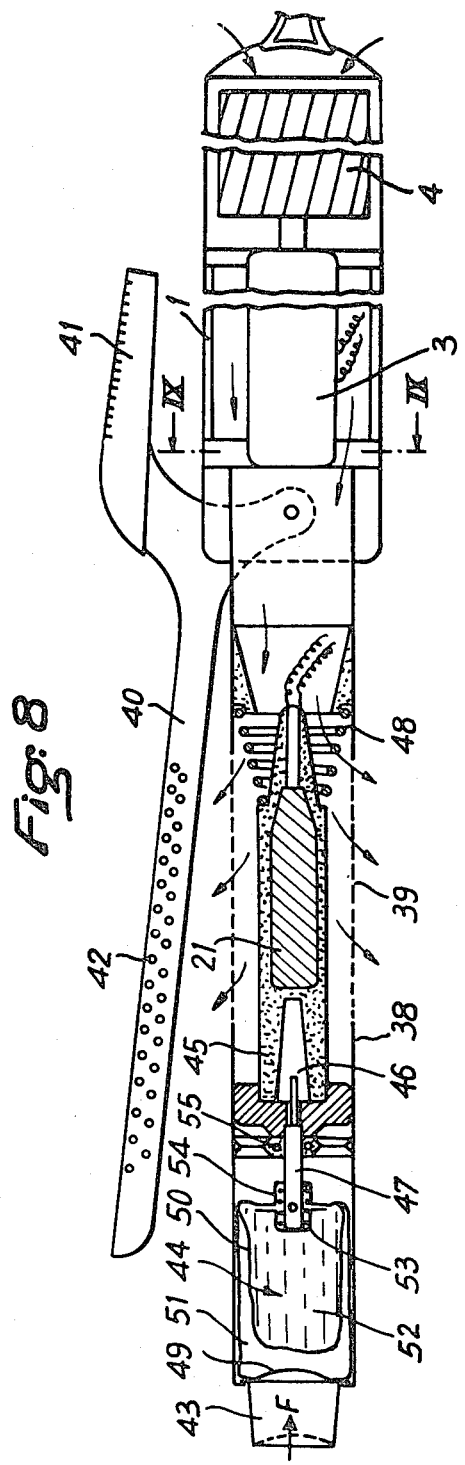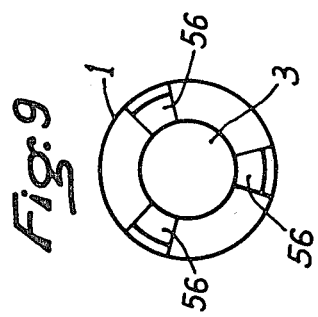

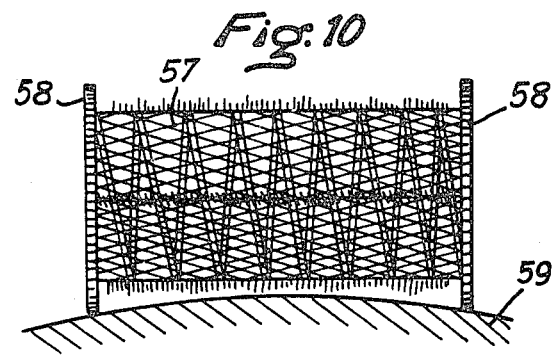
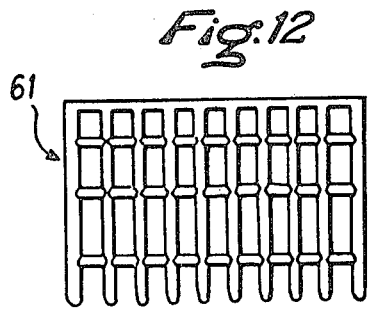
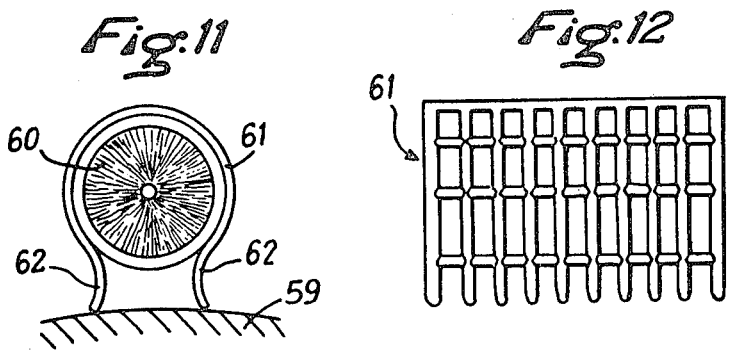
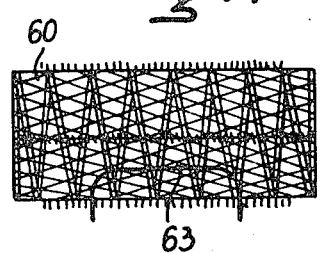
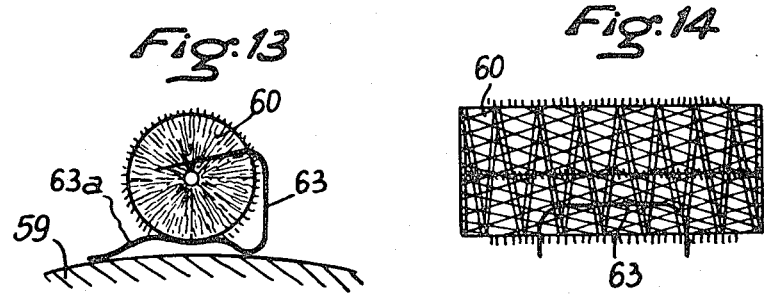
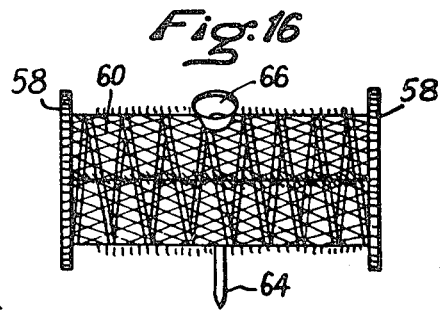
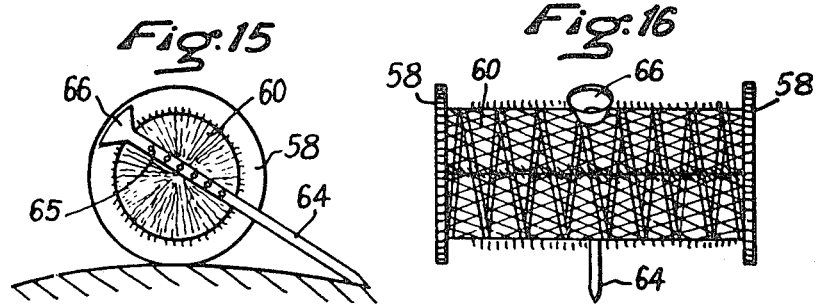

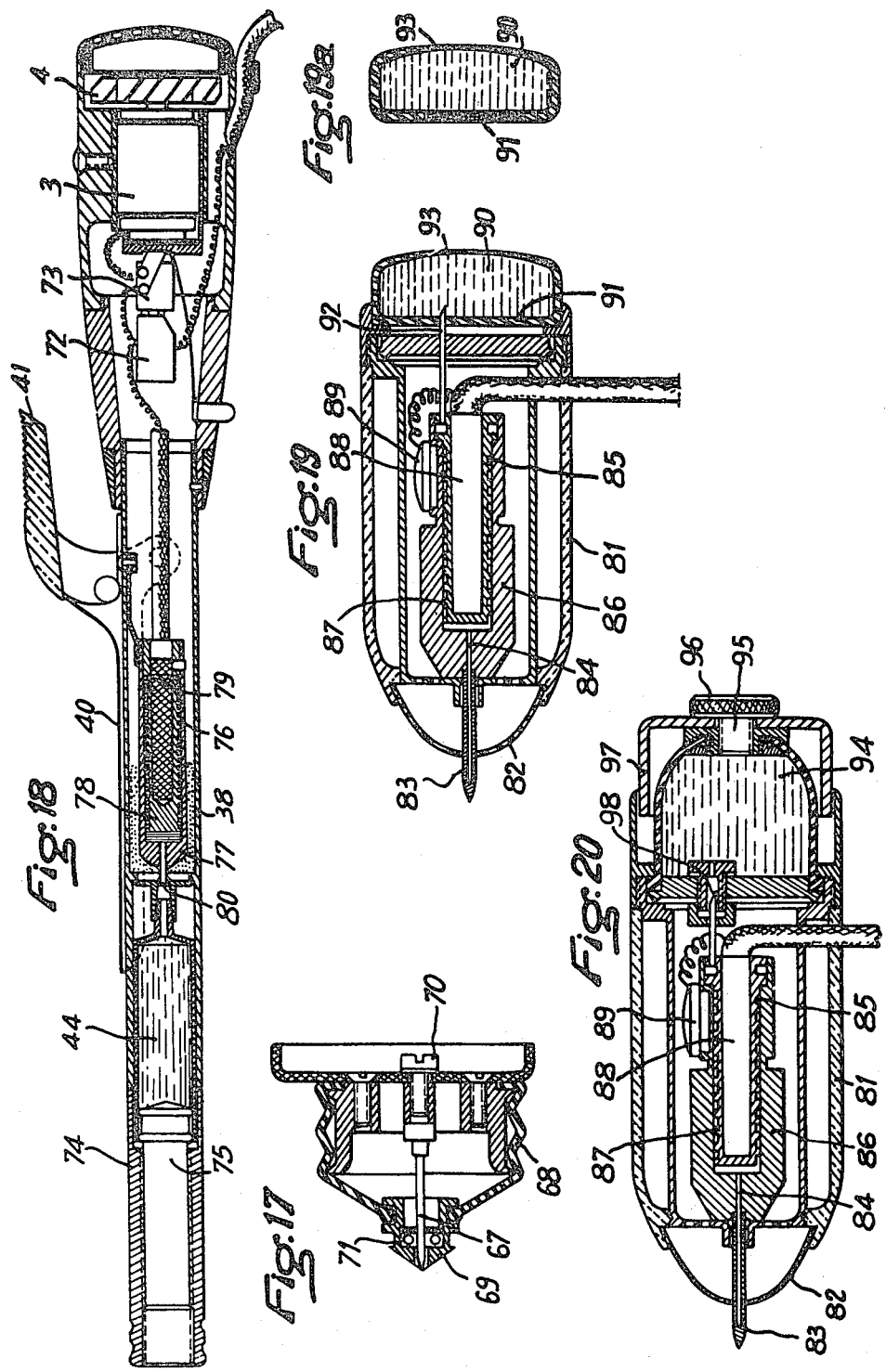

METHOD AND APPARATUS FOR SETTING HAIR

This is a division of application Ser. No. 584,980, filed June 8, 1975, now U.S. Pat. No. 4,166,473 issued Sept. 4, 1979.

SUMMARY OF THE INVENTION

This invention relates to a new process for setting or otherwise treating human hair, as well as to devices for carrying out this process.

It will be appreciated that the term "setting" refers to a process which consists in imparting a shape to the hair which is temporary in nature, that is to say, one such that when the hair is again moistened, particularly when it is shampooed, this temporary shape dissappears.

In other words, the difference between permanent waving of the hair (which implies a chemical treatment) and "setting" resides in the fact that moistening or washing the hair after it has been set causes it to return to its original shape, as it was before the setting occurred, whereas after permanent waving the shape of the hair is not altered by subsequent wetting or washing.

The setting process most commonly used consists in beginning with moist hair which is wound on rollers and then dried under a drier at a temperature between 30° and 60° C. for a length of time which may vary from 20 to 60 minutes depending upon the mass of hair to be dried. After this it is only necessary to remove the rollers and comb the hair to complete the coiffure.

Alternatively, the hair is impregnated with a setting lotion which may consist, for example, of a solution of "conditioners" such as resins, which, after drying, sheath the hair and keep it in position.

Another technique is known, which, although less common, consists in starting with dry hair which is wound on rollers and moistened with water, which may be sprayed thereon as fine drops before or after winding on rollers, or is subjected to the action of a mixture of air and steam heated to a level which the scalp will tolerate, that is to say a maximum of the order of 60° C., and propelled toward the hair by means of a blowing hood or a hand dryer.

Finally, another setting process consists in utilizing the old technique of using a curling iron to curl the hair.

In this latter process the hair is heated in a nonuniform manner to a temperature of more than 100° C. by the application of a hot metallic mandrel.

The hair may be subjected before or after the treatment to an application of steam, which may be delivered by the curling iron itself. This water may be removed by evaporation before the hair is released from the heating mandrel and this takes about 20 seconds.

These two latter processes are not widely used because they yield results which are not considered to be very satisfactory. Setting with a curling iron has, in particular, the disadvantage of treating the hair in an irregular manner and subjecting it to very different temperatures depending upon whether it is in direct contact with the heating mandrel or spaced therefrom.

It has been found from studies and tests which have been carried out by the applicant that the best results in setting the hair are obtained when the hair is heated to a uniform temperature while being kept in the shape which is to be imparted thereto, that is to say, in practice, wound on the rollers, and when they contain at the end of the application of heat a quantity of water which corresponds to the equilibrium state at the ambient temperature in an atmosphere of average humidity.

It has in effect been noted by the applicant that sets do not last very long when, after the setting application the hair must undergo either a recovery or a loss of humidity to adapt itself to the ambient hydrometric conditions.

It follows that, in accordance with the invention, in order to obtain a good set, it is most important to heat all the hair to a uniform temperature and impart thereto a controlled humidity which is substantially the same in different parts of the hair, especially at the surface and central part of the hair.

The present invention relates to a process which makes it possible to obtain in a simple and economical manner a perfectly homogeneous treatment of the hair at a sufficient temperature to obtain setting, and impart to the hair a water content which corresponds substantially to the equilibrium state with the atmosphere in which it will ultimately be placed.

It is an object of the present invention to provide a process for setting hair which is essentially characterized by the fact that the dry hair, or partially dried hair, is subjected in a uniform manner, when coiled on a tubular member or rollers, to the action of steam which has been heated to a temperature of between 100° and 150° C., for a period of about 1 to 60 seconds. The hair on said member or rollers is then cooled to the ambient temperature and then unwound.

In a first embodiment of the invention the process according to the invention may be applied to dry hair which has been wound on a tubular member of rollers, which hair has been recently washed or may even be a little dirty, in which case it is subjected during the process according to the invention to a cleaning action which nevertheless imparts brilliance thereto and eliminates the grease thereon to a substantial extent.

In a second embodiment of the process according to the invention the steam is applied to the hair wound on the tubular member or rollers, after said hair has been washed and has been first subjected to a partial drying operation, the steam being applied at a moment at which the hair is not yet completely dry.

It is a characteristic of the process according to the invention that the heating of the hair which produces the set may be obtained by the application of steam heated to a temperature of 100° to 150° C. which uniformly bathes the hair while penetrating all its fibers.

The process according to the invention is carried out without using any means for heating the hair to a high temperature acting by direct contact with the hair, but in certain applications it is possible to apply the steam at a temperature between 100° and 150° C. while the hair is wound on a cylindrical mandrel, the outer temperature of which is above the ambient temperature but which must remain at less than about 70° C., the temperature of said mandrel being substantially less than the temperature at which a setting operation is produced by modification of the hydrogen bonds of the keratin. This relatively low temperature substantially eliminates the risk of burn of the user.

In accordance with one variation of the process according to the invention, steam heated to a temperature between 100° and 150° C. is blown through the lock of hair wound on the roller, and then a current of air for example at the ambient temperature, is used to cool the hair before removing the rollers.

The process according to the invention makes it possible to provide a substantial improvement in the sets obtained, even when compared with those traditional sets which were heretofore considered the best.

There is first noted an important improvement in the durability of the set, so that the hair only returns slowly to its initial shape when subjected to a humid atmosphere.

It is also noted that the treated hair is softer, that the colors of the hair are more lively and striking and it becomes oily more slowly after the set. Moreover, especially with respect to fine hair, the hair has more body after setting in accordance with the invention.

It is also remarkable that, while the scientific literature mentions the degradation of keratin chains by steam at temperatures of 100° to 150° C., the process according to the invention, even when applied in a repetitive manner to the hair, does not produce any discernable modification of its structure.

Chemical analyses have been carried out on natural hair which has undergone 32 successive applications of the process according to the invention (using steam at 120° C. and applications of 5 seconds) without revealing any modification in its structure. The process according to the invention also has the advantage that the improvement in the properties which it imparts to the set is greater when the hair undergoes a set after having first been sensitized or degraded, for example, by bleaching or permanent waving or dyeing.

As a variation in the process according to the invention, instead of blowing steam onto the hair at a temperature of 100° to about 150° C., chemical compositions which are capable of having an action on the hair, or a mixture of steam and such compositions is blown, these compositions being for instance solutions, suspensions or azeotropes.

For example, the hair may be permanently waved, that is to say, a deformation of the hair may be produced which resists moistening or washing, by first projecting onto the hair a mixture of vapor and reducing gas and then, in a second step, a mixture of vapor and an oxidizing gas. To carry out the first step one may, for example, utilize an aqueous solution of ammonium sulphide or hydrazine, whereas a solution of hydrogen peroxide may be used for the second step.

With the process according to the invention it is also possible to use steam treatment at a temperature of 100° to about 150° C. to accelerate or cause chemical reactions by compositions which have already been placed on the hair.

It is also possible, if so desired, to produce a reaction on the hair between a composition which has already been applied to the hair and another composition which is blown onto the hair by the steam at a temperature of 100° to about 150° C.

With the process according to the invention it is also possible to use a curler or roller which comprises a spongy substance which has first been impregnated with a chemical composition which is subjected to the action of the heated vapor.

The tests which have been carried out by applicant have revealed, in a surprising manner, that the treatment with steam according to the invention in order to bring about or initiate chemical reactions on the hair has the great advantage of degrading the hair less than if the same chemical reactions were carried out in a conventional way. In the case of the invention, these reactions have a tendency to occur throughout the mass of the hair and not merely at the surface thereof, as in the case with traditional treatments.

Results are thus obtained which are superior in intensity, more rapid, and leave the surface of the hair in better shape.

Another object of the present invention is to provide a new article of manufacture which consists of an apparatus for carrying out the process according to the invention, said apparatus being characterized by the fact that it comprises in combination a vaporizer having a heating resistance, said vaporizer discharging into an ejector capable of being applied against or engaged in the hair to be treated, and a pump making it possible to withdraw into a reservoir predetermined quantities of a liquid for delivery to the vaporizer, from which it is evaporated by the ejector in the form of steam at a temperature in excess of 100° C.

The apparatus comprises in a preferred embodiment a blowing and/or sucking device adapted to direct a current of air at ambient temperature against the wound hair and/or to suck a current of air at ambient temperature through the wound hair.

In a preferred embodiment of the invention the vaporizer is equipped with a thermostat so as to control the temperature of the steam which is emitted by the apparatus.

In a preferred embodiment of the invention the vaporizer also comprises a body, which may be metallic, which contains within it heated metallic granules across which the liquid and steam which is produced by the vaporizer pass. In a first embodiment the steam injector is situated in the current of air blown by an apparatus according to the invention. In a second embodiment the steam injector is located above a ramp which permits the diffusion of fresh air. It is also possible to blow the steam directly onto the lock of hair wound on the roller while the ramp for diffusing fresh air insures the circulation of air and cooling at the level of scalp to avoid an increase in temperature due to the steam.

In its simplest form, the steam injector consists of a hollow needle, the end of which may be rounded, and which is provided near its end with a certain number of orifices which may advantageously be inclined with respect to the axis of the needle and directed to the rear.

This needle may be inserted into the roller or curler so as to open into the center of the lock of hair and create a circulation of steam which flows from the center toward the exterior so as to produce uniform treatment of the hair.

In an improved embodiment of the invention, in order to prevent the hot steam from being projected into the immediate neighborhood of the scalp due to inadvertence of the user of the apparatus, the injector is surrounded by a telescopic protective sleeve, which, when at rest, is biassed outwardly, and blocks the outlets of the injector, the vaporizer being then connected to orifices which are positioned laterally on the body of the apparatus.

In order to introduce steam into the hair, the injector is moved, together with its sleeve, in the direction of a lock of hair. The injector can penetrate into the lock but the sleeve, because of its front bearing surface, cannot penetrate and is pushed toward the inside of the apparatus. This displacement of the protective sleeve opens the orifices in the injector and blocks the lateral orifices for release of steam which are situated in the body of the apparatus. In an alternative form, the injector may consist of a diffuser which is applied to the lock of hair.

In another alternative form of the apparatus according to the invention, it is possible to introduce into the vaporization chamber water or another liquid composition which is inside a container under pressure or a disposable cartridge.

In a particular embodiment of the invention the control of the introduction of liquid into the vaporization chamber simultaneously terminates the blowing of air.

The apparatus according to the invention may be of the type in which the heated vapor is injected into a lock of hair wound on a separate curler.

It may also be of the type in which the apparatus itself constitutes a curler with the lock wound around the body of the apparatus, said lock receiving preferably in succession a supply of heated vapor, followed by a supply of air intented to cool it before release of the lock from the apparatus.

When separate curlers or waving rollers are used, it is preferable, in accordance with the invention, to avoid contact between the lock wound on the roller and the scalp so as to permit thermal isolation of the scalp. To this end it is possible to utilize devices of various types, such, for example, as curlers or setting rollers which are provided with lateral flanges or other devices for spacing them from the scalp.

It is also possible to use ordinary rollers provided with devices such as pins or supports which space them from the skin.

Finally, in accordance with the invention, it is possible to use as a curling pin or setting roller, hollow devices inside of which it is easy to insert the injector through which the steam is introduced into the roller.

In order that the invention may be better understood, several embodiments thereof will now be described, purely by way of illustration and example, with reference to the accompanying drawings, on which:

FIG. 1 is a schematic sectional view taken through a first embodiment of the device according to the invention;

FIG. 2 is a sectional view taken along the line II—II of FIG. 1;

FIG. 3 is a sectional view taken along the line III—III of the vaporizing member of FIGS. 1 and 2;

FIG. 3A illustrates an alternative form of the injection needle which may be used in the device according to the invention;

FIG. 4 is a schematic view of another form of the apparatus of FIG. 1;

FIG. 5 is a front view of the injection and diffusion head for fresh air;

FIG. 6 is a sectional view on a larger scale taken along the line VI—VI of FIG. 5, showing the structure of a safety device;

FIG. 7 is a sectional view of another form of the injector;

FIG. 8 is a schematic sectional view taken through a third embodiment of the apparatus according to the invention;

FIG. 9 is a sectional view taken along the line IX—IX of FIG. 8;

FIGS. 10 to 16 show different embodiments of rollers which may be used in carrying out the process of the invention;

FIG. 17 shows an alternative form of an injection device suitable for use in the apparatus according to the invention;

FIG. 18 is a schematic sectional view through another embodiment of the apparatus according to FIG. 8;

FIG. 19 is a schematic sectional view of another embodiment of the apparatus according to the invention;

FIG. 19A is a schematic sectional view of a recharging cartridge which may be used in the apparatus according to FIG. 19; and FIG. 20 is a schematic sectional view of another embodiment of the invention according to FIG. 19.

One embodiment of a device for carrying out the process according to the invention is schematically illustrated on FIG. 1. This device comprises a body 1 connected to a handle 2.

The body 1 has at its rear end a motor 3 equipped with a fan 4 which insures a circulation of air inside the body of the apparatus in the direction indicated by the arrows on FIG. 1. This air is drawn to the rear part of the body 1 and is delivered to the mouth 5. A vaporizing and heating member 6 is mounted within the mouth 5 inside the body 1 so that the air circulates about it.

This vaporizing member 6 is connected to a hollow needle 7 which projects from the front of the apparatus and is provided at its free end with openings 8 through which the vapor may escape.

The handle 2 is provided at its lower end with a reservoir 9 equipped with a filling plug 10. A mechanical pump 11 actuated by a trigger 12 is connected, on the one hand, by a tube 13 to the reservoir 9 and, on the other hand, by a tube 14 to the vaporizing member 6. The pump 11 is of a conventional structure and comprises two valves 15 and 16 which delivers a predetermined quantity of liquid to the vaporizing member 6 each time the trigger is pressed in the direction of the arrow F.

As may be clearly seen in FIGS. 2 and 3, the vaporizing member 6 consists of a metallic body 17 having the shape of a parallelopiped. This body is pierced by a central bore 18 opening at one end into a spigot 19 connected to the tube 14, and communicating at the other end with the hollow ejection needle 7, which is provided near its free end with openings 8 through which the heated steam is ejected.

The central orifice 18 is provided, in the illustrated embodiment, with small balls or other metal particles which permit the rapid transfer of heat to the liquid which passes through the vaporizing member.

On opposite sides of the bore 18 are two other bores 21 which contain electrical resistances supplied through wires 22.

A thermostatic device 23 positioned beneath the vaporizing member 6 makes it possible to continuously control the vaporizing temperature.

The vaporizing member 6 is mounted in the body 1 of the apparatus by means of insulating pads 24 which bear either against the wall of the body 1 or against radial supports 25.

The lateral parts of the body 17 of the vaporizing member are provided with grooves 26 to prevent too much heat from being diffused toward the body 1 of the apparatus.

In the embodiment illustrated in FIG. 3A, the injection needle 7′ has orifices 8′ which are inclined with respect to its axis toward the rear of the needle so as to still further decrease the risk of accidental injury to the scalp by the heated vapor.

It will be readily appreciated from the description which has just been given that the apparatus according to the invention always blows a current of cold air from its mouth 5 around the ejection needle 7 or 7′ and that, each time that pressure is exerted on the trigger 12, a predetermined quantity of liquid contained in the reservoir 9 is forced inside the vaporizing member 6 so that the heated vapor escapes through the orifices 8 and 8' respectively of the injection needle 7 or 7'. This apparatus makes it easy to treat the hair with heated vapor in accordance with the process according to the invention, with the flow of cold air assuring both the protection of the scalp from the vapor which is introduced into the roller and the rapid cooling of the lock of hair wound on the roller before removal therefrom.

FIG. 4 schematically shows another embodiment of the device according to the invention comprising the body 1 of the apparatus and the handle 2. The internal parts of the device such as the blowing means and the liquid pumping means have not been shown in detail because they may be of any type and one embodiment thereof has already been described. The vaporizing and heating member 6 has been schematically indicated.

This member supplies the heated vapor to an injector 27 which will be hereinafter described in greater detail. The current of air from the fan is supplied to a diffuser 28 which is best seen on FIG. 5. This diffuser consists of a slot 29 which distributes a layer of cold air propelled by a motor driven fan (not shown on the drawings). FIG. 5 also shows one embodiment comprising two injection needles 7 which are identical and positioned side by side. Of course, each of these needles is connected to the heating and vaporizing member.

It will be seen that, as a consequence of this embodiment, it is possible to introduce the two injection needles 7 into the roller on which the hair is wound while a layer of cold air is blown by the ramp 29 near the scalp, so as to avoid excessive heating of the scalp by the vapor.

FIG. 6 shows the injector 27 in section on a larger scale. This improved embodiment is designed to prevent the vapor from escaping through the injection needle, which is provided with orifices 8 as in the embodiment just described, when it is not desired to introduce the vapor into the lock of hair.

In the device illustrated in FIG. 6, the hollow injection needle 7 is surrounded by a protective sleeve 30, which is so mounted as to be telescopically slidable, and biassed by a spring 31. A stop 32 sliding in a slot 33 in the sleeve makes it possible to limit this reciprocating movement.

The outer end of the protective sleeve 30 has an enlarged head 34 the purpose of which will be hereinafter explained.

The bore 35 in which the needle 7 slides is connected to the generator of the heated vapor.

Bores such as 36 connect the lateral side of the member 27 with the bore which contains the base of the needle 7. Complementary orifices 37 in the needle permit communication between the inside of the needle (through which the heated vapor arrives) with the bores 36. In the position illustrated in solid lines of FIG. 6, in which the vapor is not being injected into the lock of hair, the protective sleeve is pushed outwardly by the spring 31 and blocks orifices 8 of the injection needle 7. On the contrary, the vapor which arrives at 35 may escape to the outside by passing through the orifices 37 and the bores 36. This escape occurs laterally so that there is no risk of burning the scalp.

On the contrary, in order to inject the vapor into the roller, the sleeve is pushed against the roller, but the enlarged head 34 of the sleeve cannot penetrate inside it and is pushed back into the position shown in broken lines while the injection needle 7 penetrates inside the roller. At the same time the orifices 8 are opened and the sliding sleeve blocks the orifices 37.

It follows that, in the position illustrated in broken lines, the heated vapor passes to the end of the injection needle and is diffused inside the roller.

Of course when the needle is withdrawn from the roller the protective sleeve returns to the position shown in solid lines on FIG. 6.

The air diffuser 29 is schematically illustrated on FIG. 6.

FIG. 7 shows an alternative embodiment of the injector 7 in which the heated steam escapes through a porous mass 7a, for example, sintered metal, instead of escaping through the orifices 8 of the needle. This results in a less rapid diffusion and greater dispersion of the heated vapor.

FIG. 8 schematically shows another embodiment of the apparatus according to the invention in which the hair which is to be treated is wound around the device whereas, in the preceding embodiment, the steam was introduced by an injector which had penetrated inside a lock of hair wound on a roller.

The embodiment of FIG. 8 comprises a motor 3 which drives a fan 4 which forces into the body of the apparatus a current of air in the direction of the arrows.

The body 1 of the apparatus which contains the motor 3 and the fan 4 is connected to a tubular member 38 provided with peripheral orifices 39. A pivotally mounted clip 40, controlled by a handle 41 and also provided with orifices 42, may be applied against the tubular body 38 or separated therefrom in the manner of conventional curling irons.

Inside the tubular part 38 is mounted an axially slidable assembly which comprises the following components:

A push button 43 adapted to initiate the injection of vapor, a cartridge 44 containing the liquid to be vaporized, and a vaporizing member consisting for example of a porous body which may be obtained by sintering.

The vaporizing member comprising an electrical resistance 21 which is preferably controlled by a thermostat (not shown) and a vaporization chamber 46 into which a duct 47 opens. This duct is connected to the reservoir 44 for liquid under pressure.

A spring 48 permanently urges this assembly to the left and holds the end of the vaporizing member 45. In the position of the components shown in FIG. 8, the air supplied by the turbine 4 passes through the coils of the spring 48. The reservoir containing the liquid under pressure consists, in the embodiment described, of a fluid-tight capsule 49 inside which there is a membrane 50 which delimits a volume 51 containing a gas under pressure, and a volume 52 containing the liquid which must be supplied to the vaporizing and heating member.

The tube 47 is fixed to a valve 53 which is closed by a spring 54. The tube 47 is itself guided by a support 55 fixed to the body of the device. The device operates as follows:

In the position illustrated the fan drives the fresh air which circulates in the direction indicated by the arrows and this fresh air is diffused through the lock of hair which is wound around the body 38 of the roller and held in place by the clip 40.

When heated vapor is to be applied to the hair it suffices to press in the direction of the arrow F on the push-button 43. Movement of the push-button toward the right first causes displacement of the assembly comprising the reservoir 44 and the vaporizing member 45, thus opening the valve 53, and at the same time progressively compressing the spring 48.

When the spring 48 is completely compressed the flow of air is completely cut off since the fan 4 is operating in a closed space. Only at this time is it possible to overcome the spring 54 and open the valve 53. The gas under pressure contained in the space 51 then expells the liquid contained in the space 52 which reaches the vaporizing chamber 46 in which it is immediately transformed into heated vapor. The vapor may escape through the porous walls of the chamber 46. It thus reaches the periphery of the vaporizing member, where it is heated and then evacuated through the orifices 39 which are located in the wall of the tubular member 38. The vapor thus heated passes regularly through the locks of hair wound around the member 38.

In order to stop the supply of vapor it is sufficient to release the pressure on the push-button 43 and the springs 48 and 54 return the various components to the positions shown on FIG. 8 and again initiate the flow of fresh air through the orifices 39 to rapidly cool the hair.

Finally, pressure on the handle 41 will release the lock of hair which was previously wound on the body 38 of the device.

FIG. 9 is a sectional view showing the wall of the body 1 of the apparatus and the motor 3 which is held in position by radial members 56 so as to permit the passage of air. It will be clearly seen that the apparatus according to the invention is fundamentally different from apparatuses of the curling iron type which utilize a flow of vapor. In effect, in an apparatus according to the invention two fundamentally distinct and different treatments are applied to the hair. In the first step, the flow of air is cut off and heated vapor supplied, whereas in the second step the emission of vapor is stopped and a flow of air at the ambient temperature is directed against the hair.

The apparatus according to the invention is distinguished from devices heretofore known by the fact that heat is never conducted from the body 38 to the hair wound thereon. In effect, in accordance with the invention, the body 38 consists of a thin metallic wall or thicker insulating wall which has a very low thermal inertia and is instantaneously brought either to the temperature of the vapor which is emitted in the vapor emission step or to the ambient temperature by the air which passes through the wall of the member 38 at a high rate of flow.

It follows that the hair wound on the member 38 of the apparatus is never subjected to heat transfer by conduction and is treated at a homogenous temperature by the mass of vapor which diffuses through the hair or is cooled by the flow of cold air.

On the contrary, in the case of the steam curling irons heretofore known, the hair was always subjected to a transfer of heat from the mandrel or the body on which they were wound, with the flow of vapor taking place intermittently.

It follows that, with the apparatus heretofore known, it was not possible to produce uniform cooling of the hair when it is positioned on the device.

It also follows that the cartridge 44, which is actuated by the push-button to modify the nature of the liquid vaporized, may be easily replaced so as to permit successive treatments with different chemical products.

Finally, FIGS. 10 and 16 show embodiments of rollers which may advantageously be used in the process according to the invention. FIG. 10 schematically shows a curler or setting roller which is made in a conventional manner comprising a cylindrical body 57 provided with pins analogous to the bristles of brushes projecting radially therefrom and adapted to retain the hair. This curler or setting roller is provided with two circular flanges 58 adapted to rest on the scalp 59 and space the hair from the scalp so as to prevent the vapor leaving the roller from subjecting the scalp to too high a temperature. The vapor is injected by inserting the injection needle through the hair wound on the roller.

The embodiment illustrated in FIGS. 11 and 12 is a roller of the conventional type 60 which, after the hair has been wound thereon, is placed in a clamp 61 which surrounds the greater part of its periphery and is provided with feet 62 adapted to rest on the scalp 59.

FIG. 12 is a side view showing the clamp 61 mounted on the roller.

In the embodiment of FIGS. 13 and 14, a pin 63 of a particular shape is used to simultaneously attach the lock of hair to the roller 60 and space the roller from the scalp 59. For this purpose the pin has a shape which is curved at 63a to lift it above the scalp.

FIG. 14 shows a U-shaped pin which serves both as a double pin and also correctly positions the roller 60 above the scalp.

In the embodiments of FIGS. 15 and 16 the lock of hair is held on the roller 60, for example, a roller provided with lateral flanges 58 as in the embodiment of FIG. 10, by a hollow needle 64 which is provided with orifices 65. In order to carry out the vapor treatment according to the invention it then suffices to insert the vapor injection needle (7, FIG. 1) into the needle 64.

A funnel 66 at the inlet to the needle 64 facilitates this insertion.

FIG. 17 shows an injection device which is particularly suitable for use in the device according to FIG. 1. This device comprises a hollow injection needle 67 adapted to be connected to the vaporizing member (not shown on FIG. 17) of the apparatus and a protective member consisting of a rubber bellows 68 and a conical spout 69. The needle 67 is mounted on the front part of the apparatus by means of a mounting member such as a screw 70 which pierces it axially. A rubber washer 71 is mounted around the needle 67 and acts to deflect the vapor emitted by the device.

FIG. 18 shows another form of the embodiment illustrated on FIG. 8. This embodiment has a motor 3 which drives a fan 4 which delivers to the inside of the body of the apparatus a current of air, as shown in the embodiment of FIG. 8.

In the embodiment of FIG. 18 there is also a commutator 72 and a reversing device 73 to reverse the direction of the rotation of the motor 3 and fan 4, the utility of which will be hereinafter explained. In the same manner as in the embodiment of FIG. 8 the body of the device which contains the motor 3 and the fan 4 and the device for reversing the direction of the motor is connected to a tubular part 38 provided with peripheral orifices. A pivotally mounted clip 40 controlled by a handle 41 and also provided with orifices may be applied against the tube or body 38 or separated therefrom as in the case of ordinary curling irons.

The tubular part 38 encloses a cartridge 44 containing the liquid to be vaporized and a vaporizing member.

The end of the cartridge 44 is provided with a dosing spout consisting of a sleeve 74 containing a piston 75 the end of which comes in contact with the liquid contained in the cartridge 44. The rod of the piston 75 is provided with peripheral threads corresponding to internal threads on the sleeve 74. The rod may be displaced by rotation of the sleeve so as to advance the piston 75 over a predetermined length in the cartridge 44, so that during utilization of the apparatus rotation of the sleeve 74 forces the piston into the cartridge so that a predetermined quantity of liquid contained in the cartridge 44 is injected into the vaporizing member.

The vaporizing member comprises a vaporizing chamber consisting of a helical passage 76 formed between an external body, for example of brass 77 and an internal body 78 also made of brass. The vaporizing member comprises an internal heating resistance, preferably controlled by a thermostat. The vaporization chamber 67 is connected to the cartridge 44 by a duct 80.

In an alternative method of using the device of FIG. 18, the flow of air supplied by the fan 4 to the mass of hair wound on the roller is not cut off while vapor is produced in the chamber 76 is being supplied by the hair derived from the liquid in the cartridge 44. At the end of the treatment, in order to accelerate cooling of the hair wound on the rollers, it is advantageous to use the reversing means of the motor to reverse the direction of rotation of the fan so that it draws air from the outside through the hair wound on the roller so that the air then passes into the body of the apparatus thus assuring a more rapid cooling of the hair and reducing the total length of the treatment.

FIGS. 19 and 20 show two forms of another embodiment of the apparatus according to the invention. The apparatus illustrated on these figures comprises an outer jacket 81 having a dome-shaped member 82 at its front end which is preferably made of flexible rubber and receives an injection needle 83 which is hollow such, for example, as the one shown on FIG. 3A and having four orifices which are backwardly directed at an angle of 45°.

The injection needle 83 is connected by a duct 84 to a vaporizer comprising a vaporization chamber 85 in the form of a helical passage defined between an external member 86 having a high thermal inertia, for example, brass and an internal member also of brass. A heating resistance 88 is located inside the member 87. A thermocouple 89 in series with the heating resistance 88 is located near the end of the chamber 85 near the inlet orifice for the liquid to be vaporized. The thermocouple is on the side of the chamber at which vaporization is produced while heating takes place at the opposite side of the chamber. This thermocouple serves to close the electrical circuit when the temperature becomes too low, that is to say when the vaporization step requires the use of too much heat.

In the embodiment of FIG. 19 the reservoir 90 is of the disposable type and comprises a container made of polyvinyl chloride, rubber or any like material. This reservoir is located at the rear of the device and has a front wall 91 pierced when the cartridge 90 is placed in position in the device by a hollow needle 92 in communication with the vaporization chamber 85.

The cartridge 90 comprises a rear part 93 on which the user of the apparatus presses to discharge a certain quantity of the liquid contained in the cartridge into the vaporization chamber through the needle 92.

Vapor is then supplied to the hair through the injection needle 83.

In the embodiment shown in FIG. 20 the reservoir 94, which is also made of a flexible material, comprises at its rear end a filling orifice 95 closed by a protective plug 96. This reservoir is located in a cylinder 97 capable of sliding with respect to the body 81 of the device.

A duct 98 leads the liquid contained in the reservoir 94 to the vaporization chamber 85.

In order to operate the device and supply a predetermined quantity of vapor through the injection needle 83, the user slides the cylinder 97 from the right to the left of FIG. 20, which compresses the flexible envelope constituting reservoir 94 and drives a predetermined quantity of liquid from the reservoir into the vaporization chamber. This liquid is then injected through the injection needle 83. The embodiment of FIGS. 19 and 20 is very simple in operation and may be used by operators who are not specialists with a high degree of safety and efficacy of treatment.

In order that the invention may be better understood a number of examples of how it may be carried out will now be described.

EXAMPLE 1

In order to set the hair while using the process according to the invention one starts with dry hair. That is to say, hair containing an average of about 5 to 20% water is wound on rollers 10 mm in diameter.

Vapor is injected at a temperature of 130° C. for a period of 5 seconds by means of a device such as the one previously described, by injecting 0.2 cm$^3$ of water in the form of heated vapor.

Tests have been made on natural hair and bleached hair. To measure the effectiveness of the process according to the invention the percentage of wave retention, also called the yield of the setting process, has been measured in each case.

This percentage of retention is determined in the following manner:

The lock before the setting treatment has a length LO measured between the roots and the tip. After a setting treatment on rollers having a predetermined diameter, if this lock is suspended vertically by its root, it is possible to measure at the end of the time $\theta$ a distance L between the roots and the curled tip of the lock. The percentage of retention is defined as the ratio $[(LO-L)/LO] \times 100$.

The greater this ratio the better the set. In order to define this ratio accurately it is necessary to carry out the measurements at predetermined temperatures and humidity, and measure the length L after a predetermined time. In all the tests made this length L was measured at the end of 2 hours at a temperature of 26° C. and a relative humidity of 55%.

In the tests made with natural hair treated in accordance with the example, the percentage of retention was between 30 and 35%, that is substantially better than the percentage obtained in the case of conventional sets, which is in general between 20 and 25%. The tests made on bleached hair have shown a percentage or retention between 35 and 40% whereas with a conventional set under optimum conditions the percentage of retention was 20 to 30% for the same hair.

In addition to this property of clearly superior holding power it was noted that the hair appeared brighter and more resilient and the impression of body was improved. It was also noted that it was slower to become greasy again. It should be noted that drying a complete head of hair in accordance with the invention takes around 10 minutes, whereas a conventional set on rollers requires about 40 minutes, which represents a considerable improvement in time and appreciable comfort for the users.

EXAMPLE 2

A set in accordance with the invention was made by first washing the hair by shampooing it in a conventional manner. The locks were then wound while still wet, that is to say, while containing more than 20% of water by weight, on rollers 20 mm in diameter.

Vapor was then injected at a temperature of 120° C. for about 10 seconds using about 0.5 cm$^3$ of vaporized water.

Drying was then completed under a hood for 20 minutes at a temperature of 25° C. A set was obtained which had a clearly better holding power than those of conventional sets.

A test thus made on natural hair exhibited a percentage of retention of 35 to 40% and a test made on bleached hair showed a percentage of retention of 40 to 45%, measured as indicated in Example 1.

EXAMPLE 3

Dry hair was set by means of the device illustrated on FIG. 18.

A lock of hair was wound around the tubular part 38 which had a diameter of 19 mm. Warm air was blown onto the lock by means of a fan for about 10 seconds. 0.5 cm$^3$ of water in the form of steam at 110° C., was injected for a period of one second. Warming was continued to eliminate any condensation for a period of about 10 seconds. The direction of rotation of the motor was then reversed so as to draw fresh air through the hair and insure complete cooling. This operation lasted about 10 seconds.

The total operation on a lock lasted for 30 seconds. Measurement of the natural hair showed a percentage of retention of 35% and measurement of the bleached hair showed a percentage of retention of 52%, which results are substantially superior to those obtained with a conventional steam curling iron which are made the same conditions of 26% and 44% respectively.

The hair also had an improved brightness and resilience.

EXAMPLE 4

The invention was used to produce straight hair, that is to say, straight hair was produced from hair which had been waved.

Rollers were used having a diameter of 50 mm and dry hair was rolled thereon. The hair was in some cases first washed and in other cases it was not. In accordance with the invention 2 cm$^3$ of steam at a temperature of 150° C. was then injected over a period of 30 seconds.

The results obtained were clearly superior to those resulting from a conventional setting with rollers of the same diameter.

EXAMPLE 5

In order to permanently wave the hair in accordance with the process of the invention, moist locks were impregnated with an aqueous solution containing 0.2% by weight of ammonium thioglycolate having a pH of 9.3.

The hair was wound on permanent waving rollers having a diameter of 6 mm. Heated steam was injected at a temperature of about 110° C. for about 1 minute. The locks of hair were then rinsed. The fixing step was then carried out in a conventional manner, either with a hydrogen peroxide solution or with a conventional oxidizing composition, in order to carry out the second permanent waving step on the hair. This process resulted in the permanent waving of the hair with a particularly satisfactory yield of curls, that is to say, with curls having a good resistance to subsequent deformation. It is remarkable that a result of this quality could be obtained with a reducing solution having a concentration as low as 0.2%.

In a variation, instead of using an oxidizing solution in the second step, it is possible to use atmospheric air according to a known process.

EXAMPLE 6

The holding power of the sets may be increased by utilizing the technique of lanthionizing the air in accordance with the process of the invention. For this purpose the moist hair is impregnated with a gel having the following composition:
lithium bromide: 26%
lithium hydroxide: 2%
hydroxyethylcellulose WP 4400: 44%

This gel has a pH value of 10.9. The hair is wound on rollers and treated by steam injection at a temperature of about 110° C. The percentage of lanthionization obtained is 20% for a steam treatment for 30 seconds and about 33% for a treatment of about 80 seconds.

EXAMPLE 7

The set is reinforced by impregnating a lock of hair with an aqueous 5% solution of glioxal. The hair wound on the rollers is dried under a hood for 30 minutes, after which it is subjected to a vapor treatment at a temperature of about 120° C. for 40 seconds. This treatment results in an improvement in the holding power of the sets. It has also been found that by utilizing the process according to the invention an improvement in the body building effect of conventional body-building agents in aqueous or hydroalcoholic solutions may be obtained. It has been found, for example, that excellent results were achieved with polymers such as:

Polymers of vinylpyrrolidone and of diallyldimethyl ammonium bromide in a 1-3% solution in water brought to a pH of 5 by adding tartaric acid;

Polymers of vinyl acetate, allyl stearate or allyloxy acetic acid in 3% solution brought to a pH of 5 by adding lactic acid;

Cyclopolymers of polydallylbromide, methyl, or dodecylammonium in solution in absolute alcohol.

It is useful to note that with these products steam treatment resulted in an improved holding power as compared with steam treatment alone, whereas the majority of polymers added by themselves produced practically no improvement along this line.

Excellent results have also been obtained by melting products deposited as powders on the dry hair or products deposited in suspension on wet hair. Carnauba wax, thymol, stearic acid, parafin, salicylic alcohol, beeswax, and colored waxes have all been used for this purpose to excellent effect.

EXAMPLE 8

Hair is dyed using an aqueous 0.25% solution of nitroparaphenylene diamine containing 5% of a dispersing agent consisting of an oleocetylic alcohol oxethylenated with 25 moles of ethylene oxide sold under the commercial trademark REMCOPAL. Hair which was previously bleached or grey hair is impregnated with this solution. The vapor of heated water is injected for about 40 seconds at a temperature of about 120° C. The hair was dyed with a particularly high dyeing power.

EXAMPLE 9

Hair was dyed with a solution containing 10 grams per liter of methylene green in an ammoniacal medium.

The hair was impregnated with this solution and rolled on rollers 30 mm in diameter. The hair was treated in accordance with the invention for a period of 30 seconds by injecting 3 cm$^3$ of steam at a temperature of 105° C. A spectacular increase in the fixing of the color was obtained in view of the fact that this color has been particularly difficult to fix.

EXAMPLE 10

The hair was reconditioned with a trimethylolmelamine in a 3% solution at pH 2 (HCl). The hair was wound on rollers 25 mm in diameter and subjected to steam treatment by 15 injections for one second of steam at 135° C. using 2 cm$^3$ of solution. Better results were obtained than with the application of the solution alone.

EXAMPLE 11

In order to permanently wave the hair, an aqueous solution of ammonium sulfite, SO$_3$(NH$_4$)$_2$, at 4% by weight was used.

This solution was introduced into the reservoir of the vapor generating device. The hair was wound on rollers and for 30 seconds the heated vapor resulting from the vaporization of the said aqueous solution was blown through hair wound on rollers 6 mm in diameter.

Hydrogen peroxide at 5 volumes (a concentration of 1½%) was then introduced into the reservoir of the vapor generating apparatus and the vapor resulting from this solution was blown through the hair for 30 seconds. This resulted in the reconstitution of the keratin bonds which had been broken by the treatment with ammonium sulfite which, by decomposition, released SO$_2$ gas and NH$_3$ gas.

This resulted in a good permanent wave for the hair. In a variation, instead of using a solution of ammonium sulfite in the first reducing step, a 5% solution of hydrazine hydrate in water may be used.

The hydrazine solution may also be used to impregnate a spongy mass located inside the roller, so that the heated vapor penetrating the spongy mass carries the treating composition into the hair. It will be noted that, in this variation, it is not necessary to resort to fixing by chemical means and the hair may be fixed by the oxygen in the atmosphere.

EXAMPLE 12

The hair is set by proceeding as indicated in Example 2 by filling the reservoir of the apparatus with an azeotropic 9% solution of benzyl alcohol and water. After treatment, the holding power of the set is just as good as in the case of steam only as in Example 2 and there is in addition a significant improvement in the ease with which the dry hair may be untangled. There was no residual odor, and an improved brightness

EXAMPLE 13

The hair was set in accordance with Example 1 by introducing into the reservoir a 1.6% solution of diethyl phthalate in water. The holding power of the resulting set was as good as in the case of steam alone and it was also noted that there was an approximately 9% improvement in the coefficient of friction of the hair.

EXAMPLE 14

The hair was set as in Example 2 but the reservoir of the device was filled with hydrogen peroxide at 6 volumes and the hair was impregnated before steam treatment with a solution having the following composition:
thioglycolic acid: 0.5%
copolymer of vinylacetate and crotonic acid: 1.5 g
pH: 2.6
water, q.s.p.: 100 cm$^3$ This resulted in excellent holding power with a light permanent wave despite the very low thiol concentration.

EXAMPLE 15

The hair was set as in Example 2, the reservoir of the device according to the invention being filled with hydrogen peroxide at 3 volumes and the hair being impregnated before treatment with the steam by a lotion having the following composition:
thiolactic acid: 0.2%
copolymer of vinylacetate and vinylpyrrolidone: 2 g
pH: 2.9
water, q.s.p.: 100 cm$^3$ This resulted in a very good holding power, superior to that obtained with a body building lotion.

It will of course be appreciated that the embodiments which have just been described have been given purely by way of example and may be modified as to detail without thereby departing from the basic principles of the invention. In particular, it is obvious that the process according to the invention is not limited to the setting of hair but may also be applied to all sorts of vapor treatment which permit the effectuation of all sorts of chemical reactions on the hair, such as permanent waves, dyeing, strengthening, or body building treatments.

It is also obvious that the process according to the invention is not limited to the case of setting or treatments carried out on setting rollers, but may be also used when it is desired to set or treat curled hair which must be wholly or partially straightened as will be seen from reading Example 4.

What is claimed is:

1. A process for setting hair which comprises the steps of subjecting at least partially dry hair wound on a tubular member to the action of steam at a temperature between 110° and 150° C. for a period of 1 to 60 seconds, without substantially otherwise heating the hair, and unwinding the hair from the member only after the hair is cooled to about ambient temperature.

2. A process for setting hair according to claim 1, wherein said step of subjecting the hair to the action of steam comprises, subjecting the hair to successive short bursts of steam.

3. Process for treating the hair which comprises the step of injecting steam at 110° to about 150° C. into the hair, to add moisture to the hair without wetting the hair and in which said steam contains gaseous chemical compositions adapted to modify the properties of the hair.

4. Process as claimed in claim 3 in which the hair is first treated with steam containing a gaseous reducing agent and then with steam containing a gaseous oxidizing agent so as to permanently wave the hair.

5. Process of treating the hair in which steam at 110° to about 150° C. is introduced into hair to add moisture to the hair without wetting the hair which has been first impregnated with a chemical solution or is wound on rollers which have been impregnated with a chemical solution.

* * * * *

UNITED STATES PATENT AND TRADEMARK OFFICE
CERTIFICATE OF CORRECTION

PATENT NO. : 4,341,229

DATED : July 27, 1982

INVENTOR(S) : Daniel Bauer et al.

It is certified that error appears in the above-identified patent and that said Letters Patent is hereby corrected as shown below:

On the title page add:

[30] Foreign Priority Data:

June 10, 1974       Luxembourg        70,281

Item [62], "Jun. 8, 1975" should read -- Jun. 9, 1975 --.

Signed and Sealed this

Twenty-third Day of August 1983

[SEAL]

Attest:

GERALD J. MOSSINGHOFF

Attesting Officer     Commissioner of Patents and Trademarks